United States Patent
Sandel et al.

(10) Patent No.: US 8,800,766 B2
(45) Date of Patent: Aug. 12, 2014

(54) SHARPS CONTAINER FOR REMOVING AND CONTAINING BLADES FROM ROUND SCALPEL HANDLES

(75) Inventors: Dan Sandel, Malibu, CA (US); Tonya Fambrough, Dickson, TN (US)

(73) Assignee: Ansell Limited, Victoria (AU)

( * ) Notice: Subject to any disclaimer, the term of this patent is extended or adjusted under 35 U.S.C. 154(b) by 32 days.

(21) Appl. No.: 13/555,747

(22) Filed: Jul. 23, 2012

(65) Prior Publication Data

US 2013/0019567 A1 Jan. 24, 2013

Related U.S. Application Data

(60) Provisional application No. 61/510,956, filed on Jul. 22, 2011.

(51) Int. Cl.
| | |
|---|---|
| *B65D 83/10* | (2006.01) |
| *A61B 17/32* | (2006.01) |
| *A61B 17/3217* | (2006.01) |
| *A61B 17/06* | (2006.01) |
| *A61B 19/00* | (2006.01) |
| *A61M 5/32* | (2006.01) |
| *A61B 19/02* | (2006.01) |

(52) U.S. Cl.
CPC ... *A61B 17/06161* (2013.01); *A61B 2019/4821* (2013.01); *A61M 2005/3206* (2013.01); *A61B 17/3217* (2013.01); *A61B 2019/0232* (2013.01); *A61B 2019/0209* (2013.01); *A61B 19/0288* (2013.01)
USPC .......................................... 206/370; 606/167

(58) Field of Classification Search
USPC ............ 206/363–370, 438, 570–572; 29/239; 606/167
See application file for complete search history.

(56) References Cited

U.S. PATENT DOCUMENTS

| | | | |
|---|---|---|---|
| 4,013,109 A | 3/1977 | Sandel | |
| 4,318,473 A | 3/1982 | Sandel | |
| 4,736,844 A * | 4/1988 | Scott et al. ................... | 206/370 |
| 4,842,138 A | 6/1989 | Sandel et al. | |
| 5,024,326 A | 6/1991 | Sandel et al. | |
| 5,112,314 A | 5/1992 | Aragon et al. | |
| 5,449,068 A | 9/1995 | Gharibian | |
| 5,607,403 A | 3/1997 | Kretzschmar et al. | |

(Continued)

FOREIGN PATENT DOCUMENTS

| | | |
|---|---|---|
| EP | 0569233 A1 | 11/1993 |
| RU | 2290210 C2 | 12/2006 |

OTHER PUBLICATIONS

Build your own safety kit "Change-a-Blade" brochure from Sandel Medical Industries, LLC., 2 pages/.

(Continued)

*Primary Examiner* — Bryon Gehman
(74) *Attorney, Agent, or Firm* — Moser Taboada

(57) ABSTRACT

A method and apparatus for removing and containing a blade from a round scalpel handle comprising a sharps container having a wall portion that defines one side of a containment volume; a slot of a first type having a length and width dimensioned to receive a blade mounted around scalpel handle and prevent its rotation, the slot of the first type formed through the wall portion of the sharps container which slot allows rotation of the handle so the blade becomes disengaged from the handle and disposed in the containment volume.

20 Claims, 3 Drawing Sheets

(56) References Cited

U.S. PATENT DOCUMENTS

| | | | |
|---|---|---|---|
| 5,699,908 A | 12/1997 | Frye et al. | |
| 5,729,879 A * | 3/1998 | Hoftman | 29/239 |
| 5,875,532 A | 3/1999 | Musgrave et al. | |
| 5,938,027 A | 8/1999 | Soroff et al. | |
| 6,605,100 B1 * | 8/2003 | Shan et al. | 606/167 |
| 6,648,857 B1 | 11/2003 | Pedigo | |
| 6,659,277 B2 | 12/2003 | Coletti et al. | |
| 7,155,795 B2 | 1/2007 | Abidin et al. | |
| 7,398,880 B2 | 7/2008 | Henry | |
| 7,721,447 B2 | 5/2010 | Co | |
| 7,837,034 B2 * | 11/2010 | Clegg et al. | 206/366 |
| 2006/0042977 A1 | 3/2006 | Sandel | |
| 2006/0258991 A1 | 11/2006 | Lin | |
| 2007/0039844 A1 * | 2/2007 | Zyzelewski et al. | 206/363 |
| 2007/0191769 A1 | 8/2007 | Meittunen | |
| 2011/0042253 A1 | 2/2011 | Levine | |
| 2011/0226645 A1 | 9/2011 | Kierce et al. | |

OTHER PUBLICATIONS

PCT Written Opinion and International Search Report mailed Oct. 23, 2012 for PCT Application No. PCT/US2012/047848.

Sharps Safety Station TM;—www.amiwelisten.com; PS2940-AUS-CA 5000; Copyright AMI 2006.

Beaver Mini-Blades; Beaver-Visitec International, Inc.; www.beaver-visitec.com; Copyright of Beaver-Visitec International Company 2011 (BVI).

* cited by examiner

US 8,800,766 B2

SHARPS CONTAINER FOR REMOVING AND CONTAINING BLADES FROM ROUND SCALPEL HANDLES

CROSS-REFERENCE TO RELATED APPLICATIONS

This application claims priority to U.S. Provisional Patent Application Ser. No. 61/510,956, filed Jul. 22, 2011, which is incorporated by reference herein in its entirety.

BACKGROUND

1. Field

Embodiments of the present invention generally relate to a sharps container, and more particularly, to a sharps container for removing and containing a plurality of types of sharps including blades from round scalpel handles.

2. Description of the Related Art

The U.S. Department of Labor reports that due to unsafe needle devices and improper handling of needles and other sharps (e.g., scalpel blades), hospital employees are subject to a significant hazard from blood borne pathogens. According to the Centers for Disease Control and Prevention (CDC), each year, hospital employees incur approximately 385,000 sharps injuries.

Accordingly, various devices are currently in use to improve user safety and efficiency with respect to the use and disposal of sharp surgical instruments ("sharps"), such as suture needles, hypodermic needles and scalpel blades.

Current sharps remover/container designs comprise a device enabling single-handed removal of a specific type of surgical blade that is coupled to a containment volume for containing the removed sharp, i.e., enabling removal and disposal of a surgical blade from a handle without touching the blade. Such blades are generally removably attached to a reusable scalpel handle. As is well known, such surgical blades have an elongate slot centered in their rear portion that is dimensioned to releasably engage a tang or raised landing in the handle portion, so as to enable a secure, yet removable, press-fit attachment of the blade to the handle. The remover/container disengages the blade from the handle and the disengaged blade drops into the containment volume.

Surgical blades are also mounted in round scalpel handles (RSH). One such RSH blade is a BEAVER® blade available from BEAVER Visitec International of Waltham, Mass. Other manufactures make similar blades for an RSH. An RSH blade is any scalpel blade of the type that is removably secured to a round handle by a chuck or collet. Rotation of the handle causes the chuck to close about a mounting portion of the blade. Rotating the handle in the opposite direction opens the chuck and releases the blade from the RSH. Although there are sharps containers that facilitate removal and containment of standard (scalpel blades, needles, sutures, and the like, there are no sharps containers for removing and containing an RSH blade.

Therefore, there is a need for a device that enables removal and disposal of blades from round scalpel handles.

SUMMARY OF THE INVENTION

An apparatus and/or method for removing and containing a plurality of types of sharps including blades from round scalpel handles substantially as shown in and/or described in connection with at least one of the figures, as set forth more completely in the claims.

Various advantages, aspects and features of the present disclosure, as well as details of an illustrated embodiment thereof, will be more fully understood from the following description and drawings.

Figure 1:
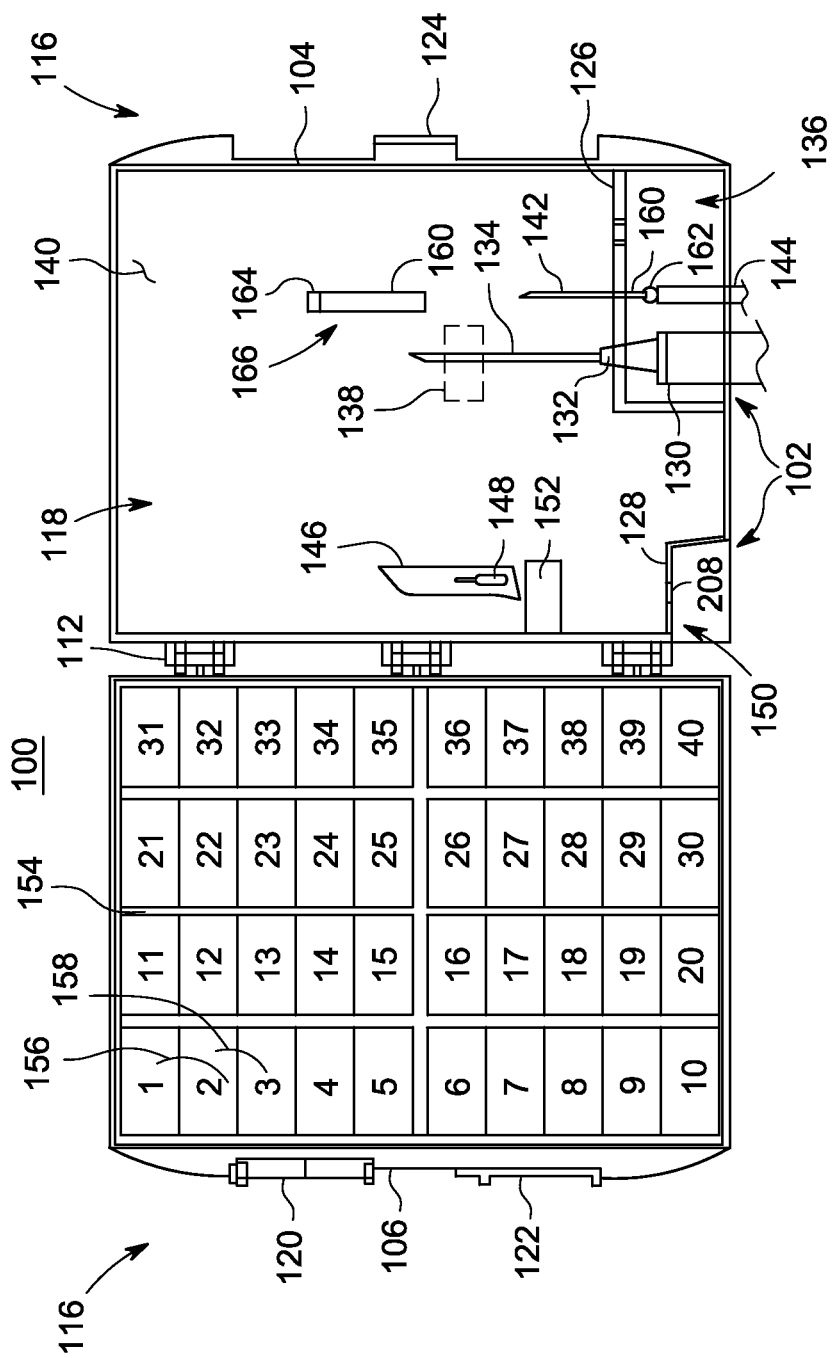
FIG. 1 is a top plan view of a sharps container including apparatus that enables removal and containment of a plurality of sharps types including blades from round scalpel handles, according to one or more embodiments.

While the method and apparatus described herein is by way of example for several embodiments and illustrative drawings, those skilled in the art will recognize that the method and apparatus for removal and disposal of sharps is not limited to the embodiments or drawings described. It should be understood, that the drawings and detailed description thereto are not intended to limit embodiments to the particular form disclosed. Rather, the intention is to cover all modifications, equivalents and alternatives falling within the spirit and scope of the method and apparatus for single-handed removal and disposal of sharps as defined by the appended claims. Any headings used herein are for organizational purposes only and are not meant to limit the scope of the description or the claims.

The word "may" is used in a permissive sense (i.e., meaning having the potential to), rather than the mandatory sense (i.e., meaning must), and the words "include", "including", and "includes" mean including, but not limited to.

Furthermore, throughout the drawings, like reference numerals will be understood to refer to like parts, components and structures.

DETAILED DESCRIPTION OF EMBODIMENTS

Embodiments of the present invention generally comprise a method and apparatus for removal and containment of various sharps, including, for example, hypodermic needles, surgical scalpel blades and/or round scalpel handle (RSH) blades. One embodiment comprises a sharps removal and containment apparatus comprising a sharps container defining a containment volume, and at least one sharps removal element formed in the sharps container, where the at least one sharps removal element is adapted for removing an RSH blade In some embodiments, the sharps container may comprise a plurality of sharps removal elements, where each sharps removal element is adapted for removing a different type of sharp and enables the removed blade to become disposed in the containment volume.

Figure 2:
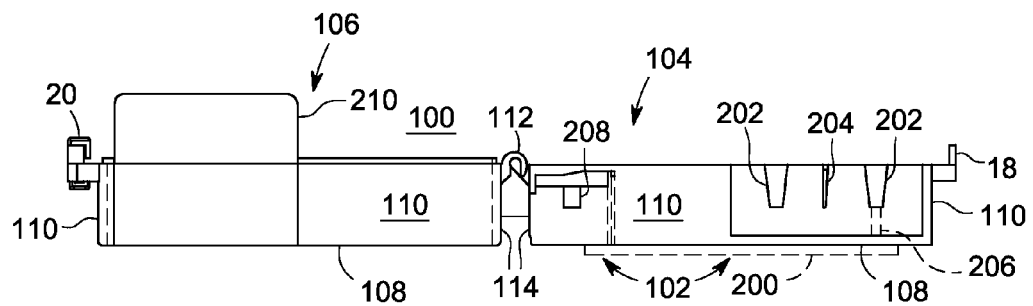
FIG. 2 is a side plan view of the sharps container of FIG. 1.
Figure 3:
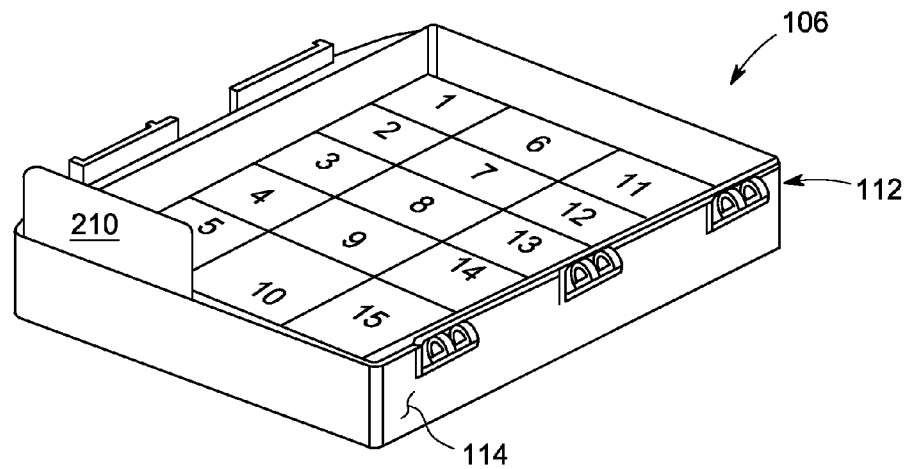
FIG. 3 is a perspective view of a top part of the sharps container of FIG. 1, according to one or more embodiments.
Figure 4:
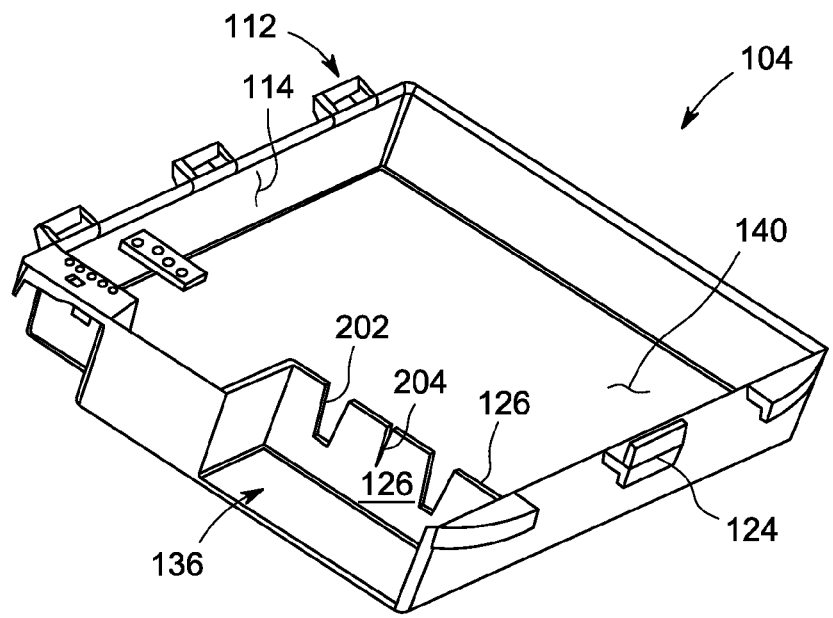
FIG. 4 is a perspective view of a bottom part of the sharps container of FIG. 1, according to one or more embodiments.
Figure 5:
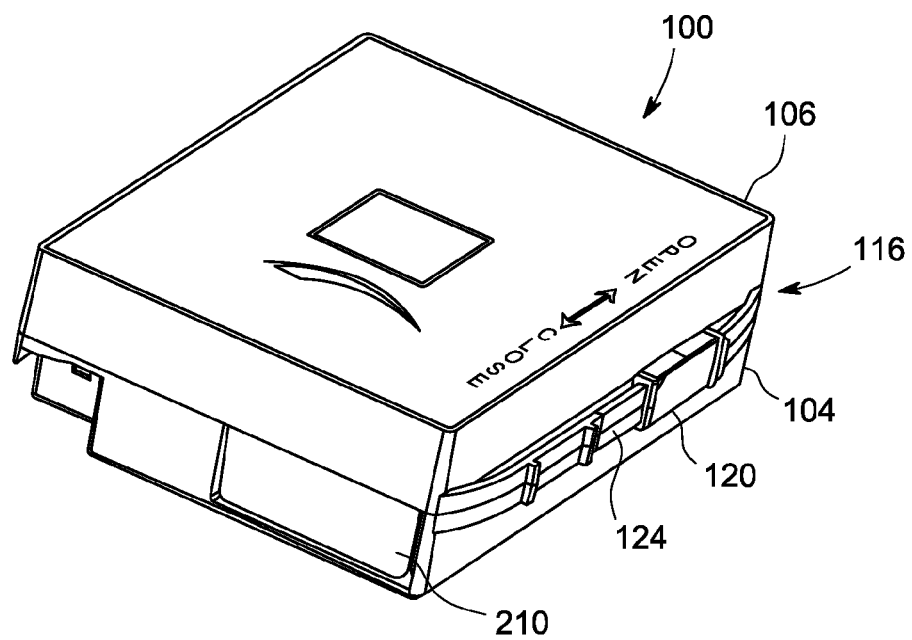
FIG. 5 is a perspective view of a closed, fully assembled sharps container of FIG. 1, according to one or more embodiments.

FIGS. 1 and 2 illustrate a top plan view and side plan view, respectively, of a sharps container 100 including at least one sharps removal element 102 that enable removal and containment of a variety of sharps, including, RSH blades, according to one or more embodiments, while FIGS. 3 and 4 illustrate perspective views of individual portions 104 and 106 of the sharps container 100 of FIG. 1, according to one or more embodiments. FIG. 5 is a perspective view of the sharps container 100 of FIG. 1 being in a closed configuration according to one or more embodiments.

As shown in these Figures, a sharps container 100 is formed of a lower part 104 and an upper part 106, each of which include a bottom portion 108 and perimeter wall portions 110. In one embodiment, the upper and lower parts 104 and 106 are fabricated of molded plastic; although, other materials may be used. Each of lower and upper parts 104 and 106 have a hinge mechanism 112 formed along one perimeter wall portion 114 and a closure mechanism 116 formed along an opposite perimeter wall portion 110. The hinge mechanism 112 allows the lower and upper parts 104 and 106 to be releasably engageable along adjacently positioned wall portions 114. As such, the parts 104, 106 can be separable if desired during a surgical procedure, and upon finishing of the procedure, the lower and upper parts 104 and 106 may be joined by the hinge 112 and then folded one on top of the other into a closed configuration, as shown in FIG. 5.

When closed, the upper and lower parts define an internal containment volume 118 within which sharps instruments, once removed from syringes, handles, and such, as described below, are contained. The specific shape, size, and volume of the containment volume 118 is considered a design choice.

In one embodiment, the closure mechanism 116 may comprise a slide 120 and a rail 122. The slide 120 may be slid along the rail 122 of the closure mechanism on part 106 so as to engage a post 124 of the closure mechanism 116 on part 104. As such, the closure mechanism 116 to thereby selectively lock the lower and upper parts 104 and 106 together, thus entrapping contents therein for disposal according to safety standards. While the two parts 104 and 106 are open, the interior area of container 100, can be used for temporary storage of sharps instruments during a surgical procedure, as well as easy disposal and accountability of used sharps instruments at the end of the surgical procedure, as next described.

To enhance stability of the container 100 when being used, one embodiment of the invention comprises an optional adhesive layer 200 positioned on the bottom surface 108 of bottom part 104. The adhesive layer 200 may comprise, for example, double stick foam, adhesive tape, hook and loop fastener, and the like. Such an adhesive layer 200 provides stability for the container 100, but is removable from a work surface when disposal or repositioning of the container 100 is desired.

As shown in FIGS. 1 and 2, a plurality of sharps removal elements 102 may be provided in recessed wall portion 126 of lower part 104, or other wall portions 110 of the container 100, in order to provide for temporary storage, removal and disposal of hypodermic needles and various blades used in a sterile surgical field.

More specifically, wall portion 110 of lower part 104 comprises a first recessed wall portion 126 and a second recessed wall portion 128.

In one embodiment, a slot 204 is formed in first recessed wall portion 126. Using slot 204, a RSH blade 142 releasably attached to a handle 144 via a rotational connection,(e.g. Chuck) is selectively removable from the handle. The slot 204 has a length and width dimensioned to receive an RSH blade 142 therein and prevent its rotation while at the same time not receive therein any portion of a handle 144 retaining the RSH blade 142.

In use, to remove and dispose of a RSH blade 142, the RSH blade 142 is placed in the slot 204 so at least a portion of the blade 142 is positioned inside the containment volume 118 and then the handle 144 is rotated so as to disengage the blade 142 from the handle 144. Conveniently, such removal of the RSH blade 142 is accomplished using only one hand, i.e., single-handed BEAVER blade removal. Upon such disengagement, the RSH blade 142 becomes discarded into the containment volume 118 of the container 100.

More specifically, when it is desired to remove a RSH blade 142 from its handle 144 for disposal and accounting, single-handed removal is provided by placing the RSH blade edgewise in the slot 204 (or slot 206) so the sharp portion of the blade is positioned into the enclosed disposal area of the container 100 while the rear portion 160 is positioned outside of the containment volume 118. Next, using the fingers of only one hand, a twisting motion is applied to the handle 144 so as to rotate the handle 144 in a counterclockwise direction, thereby causing the handle 144 to loosen its grip upon the blade. Upon reaching sufficient loosening, the blade 142 is released from a chuck 162 (or collet) and allowed to fall into the containment volume 118. In one embodiment, the inside area of bottom part 104 includes a magnetic mat 140 adhered thereto, so as to magnetically attract and keep released blades safely inside the containment volume 118. Note, an already disposed RSH blade 166 identical to blade 142 is also shown in FIG. 1, where disposed blade 166 is adhered to mat 140 and in its top view shows a flat shank portion 160 and a chisel-shaped tip portion 164. As noted above, RSH blades of other shape are also contemplated for use in the illustrated embodiments.

In another embodiment the first recessed wall portion 126 may include one or more tapered slots 202 formed therethrough. Slots 202 are dimensioned to firmly engage the disposable tip portion 130 of a syringe (portion 130 is shown). The disposable tip portion 130 typically comprises a plastic hub portion 132 having a metallic needle 134 embedded in the hub 132. The hub 132 releasably attaches to a syringe 130 by means of a press-fit or a twist-on fit, such fittings typically referred to as "Luer Lock" connections. Slot 202 allows the needle 134 to be safely positioned inside the containment volume 118 of container 100 while the remainder of the syringe is awaiting use during a surgical procedure. First recessed wall portion 126 is recessed into the containment volume 118 so as to form a resting area 136 where scalpels and syringes can be temporarily placed during a surgical procedure while having the sharp supported and extend into the containment volume 118. When it is decided to dispose of the hub portion 132, single-handed removal is possible by firmly pressing on the syringe 130 to securely engage the hub 132 in the slot 202, and then rotating or pulling on the syringe 130 by applying a separation force thereto, to cause separation of the hub 132 from the syringe 130. Upon separation, the hub 132 can be lifted by the user to dislodge it from the slot 202 and cause it, with the needle 134, to become positioned in the containment volume 118 of container 100, along with the other sharps instruments that have been positioned therein for disposal.

In an alternative embodiment, a non-coring foam block 138 may be adhered within the containment volume 118 that is opposed to and spaced a distance from the first recessed wall portion 126. The foam block 138 is positioned less than the typical distance of the length of a needle 134 to allow the user to insert the needle 134 into the foam block 138. The foam block 138 establishes additional friction between the syringe tip and the body of the syringe to assist in its safe removal from the syringe 130. In one embodiment, the block 138 may be positioned a distance from the first recessed wall portion 126 that is 50%-90% of the typical length of a needle 134. Additionally, the foam block 138 may be positioned at a vertical height above a mat 140 that is, for example, 40% to 70% of the height of the perimeter wall portions of container 100.

In a further alternative embodiment, a slot 206 may be optionally positioned to be substantially centered at the bottom of a slot like 202, thus, enabling a combined slot 202/206 to be used in place of either one or both of slots 202 or 204 for disengaging and discarding either a RSH blade and/or a syringe needle after its use.

In some embodiments container 100 may also include means for safe removal of standard scalpel blades. One such standard blade 146 is shown in FIG. 1. In one embodiment, a scalpel blade removal element 150 comprises a T-shaped slot 208 formed in the second recessed wall portion 128 and an abutment 152. Such a scalpel blade removal element 150 is described in detail in U.S. Pat. No. 4,318,473, herein incorporated by reference in its entirety. As is well known in the art, standard blades 146 have an elongate slot 148 in their rear portion, which is releasably engageable by a tang at an end of the scalpel handle (not shown) by linear displacement between the blade and tang. Upon single-handed placement of the blade 146 when attached to the scalpel handle into removal element 150, the tang of the handle can be linearly displaced with respect to the blade 146 by pressing the tang of the scalpel handle into the lower portion of slot 208 and positioning a tip of the blade 146 below the abutment 152. Upon such downward pressure, the shoulders of the slot 208 prevent the rear portion of blade 146 from moving toward the lower portion of slot 208 thereby establishing a linear displacement between the slot 148 in blade 146 and the tang portion of the handle. This displacement enables the tang of the handle to be disengaged from blade 146 while the handle is removed from slot 208, and at the same time, the blade 146 advantageously falls onto the magnetic mat 140 of the containment volume 118 of container 100 where the blade 146 is retained.

As also shown in FIG. 1, the upper part 106 of container 100 may also provide for safe and single-hand disposal, with accountability, of suture needles. More specifically, a foam block 154 is adhered within the area enclosed by the floor 108 and perimeter walls 110 of part 106, which foam block 154 may have markings to indicate a plurality of separately numbered areas. Markings 1 through 40 are illustrated, but more or less can be provided as desired. Upon desire to dispose of a suture needle, the tip of the needle is inserted into a numbered area in the foam block, as shown for sutures 156 and 158.

An extended flap portion 210 is also shown in FIGS. 2, 3 and 5, which, when parts 104 and 106 are folded together, lies adjacent to first recessed wall portion 126 of part 104. Accordingly, flap portion 210 operates to the sharps removal elements 102 in recessed wall portion 126 and thereby prevent the discarded sharps contents in container 100 from escaping the containment volume 118 via slots 202 and 204.

Thus, the sharps container shown and described herein can safely and with accountability provide not only single-handed removal of RSH blades, but also standard scalpel blades, suture needles, and hypodermic needles, thereby making it an all inclusive sharps container.

The foregoing description, for purpose of explanation, has been described with reference to specific embodiments. However, the specific embodiments are not intended to be exhaustive or to limit the invention to the precise forms disclosed.

Many modifications and variations are possible in view of the above teachings. For example, the slots 202 and 204 may have other shapes and/or be positioned in other portions of the perimeter walls 110 of the container 100, as long as the other shapes and/or position do not hinder the described function required for the slot.

The illustrated embodiments were chosen and described in order to best explain the principles of the present disclosure and its practical applications, to thereby enable others skilled in the art to best utilize the invention and various embodiments with various modifications as may be suited to any particular use contemplated. Further embodiments of the invention may be devised without departing from the basic scope of disclosure herein, and the scope thereof is to be determined by the claims that follow.

The invention claimed is:

1. Apparatus for enabling removal and disposal of a blade from a round scalpel handle (RSH), comprising: a sharps container defining a containment volume; at least one sharps removal element formed in the sharps container, where the sharps removal element is adapted for removing a blade from a round scalpel handle and enabling the removed blade to become disposed in the containment volume, wherein the sharps container comprises at least one wall portion and the at least one sharps removal element comprises a slot of a first type having a length and width dimensioned to receive and engage an RSH blade therein to prevent rotation of the RSH blade while allowing rotation of the round scalpel handle (RSH), wherein the rotation of the round scalpel handle (RSH) removes the RSH blade.

2. The apparatus of claim 1 wherein the slot of the first type is formed through the wall portion of the sharps container which slot allows rotation of the handle so the blade becomes disengaged from the round scalpel handle and disposed in the containment volume.

3. The apparatus of claim 1 wherein the sharps container comprises at least one wall portion and the at least one sharps removal element further comprises a slot of a second type having a length and width dimensioned to receive a syringe tip so as to grip the syringe tip by an amount sufficient to enable a separation force to be applied between the syringe tip and a syringe, to disengage the syringe tip from the syringe and dispose of the syringe tip in the containment volume.

4. The apparatus of claim 3, wherein the slot of the second type comprises a tapered rectangular slot, and the slot of the first type comprises a narrow slot located at a bottom portion of the slot of the second type.

5. The apparatus of claim 3, wherein the wall portion of the sharps container includes at least one slot of the second type positioned at either side of a slot of the first type.

6. The apparatus of claim 1 wherein the sharps container comprises: a first sharps removal element comprises a slot of a first type having a length and width dimensioned to receive a scalpel blade therein and prevent its rotation, the slot of the first type formed through a wall portion of the sharps container which slot allows rotation of the round scalpel handle so the blade becomes disengaged from the handle and disposed in the containment volume; and a second sharps removal element comprises a slot of a second type having a length and width dimensioned to receive a syringe tip so as to grip the syringe tip by an amount sufficient to enable a separation force to be applied between the syringe tip and a syringe, to disengage the syringe tip from the syringe and dispose of the syringe tip in the containment volume.

7. The apparatus of claim 6, wherein the sharps container comprises: a slot of a third type different from the first type and second type and having a length and width dimensioned to receive both a scalpel blade and a portion of a handle therein, which slot of the third type allows disengagement of the scalpel blade of the third type from the handle of a third type and disposal of the scalpel blade of the third type in the containment volume.

8. The apparatus of claim 1, wherein the sharps container comprises: an upper part and a lower part, each part including a corresponding hinge portion, the hinge portions enabling the upper and lower parts to become folded with respect to each other to further define the containment volume.

9. The apparatus of claim 8, wherein the upper part of the sharps container includes a raised wall portion forming a flap and the lower part of the sharps container includes a wall portion with the slot of the first type formed there through, wherein upon folding of the upper and lower parts to form the containment volume, the flap becomes aligned with the wall portion with the slot of the first type so as to complete the perimeter of the containment volume, thereby preventing escape of contents of the containment volume via the slots.

10. The apparatus of claim 1 wherein the RSH blade is a scalpel blade removably secured to the round scalpel handle by a chuck or a collet, wherein rotation of the round scalpel handle causes the chuck or the collet to either secure or release a mounting portion of the RSH blade.

11. Apparatus for enabling removal and disposal of blades from round scalpel handles (RSH), comprising: a sharps container defining a containment volume; a sharps removal element comprising a slot of a first type having a length and width dimensioned to receive and engage a RSH blade therein to prevent rotation of the RSH blade while allowing rotation of the round scalpel handle (RSH), the slot of the first type formed through a wall portion of the sharps container which slot allows rotation of a round scalpel handle coupled to the blade so the blade becomes disengaged from the handle and disposed in the containment volume.

12. The apparatus of claim 11 wherein the slot of the first type is configured to accept a RSH blade.

13. A sharps container apparatus, comprising
a plurality of interconnected floor and wall portions that define, on one side thereof a containment volume, and on an opposite side thereof an outside area;
a slot of a first type having a length and width dimensioned to receive and engage from a round scalpel handle (RSH), a round scalpel handle (RSH) blade therein to prevent rotational movement of the RSH blade while allowing rotation of the round scalpel handle (RSH), the slot of the first type formed through at least one wall portion of the sharps container for causing, upon rotational movement of the round scalpel handle, single-handed disengagement of the RSH blade from the round scalpel handle and disposal of the RSH blade in the containment volume;
a slot of a second type having a length and width dimensioned to receive a hypodermic syringe tip therein in a manner so as to grip the hypodermic syringe tip by an amount sufficient to enable a separation force to be applied between the syringe tip and a syringe, the slot of the second type formed through at least one wall portion of the sharps container for causing, upon application of a separation force between the syringe tip and the syringe, single-handed disengagement of the syringe tip from the from the syringe; and
a slot of a third type having a length and width dimensioned to receive both a scalpel blade of a third type and a portion of a handle of a third type therein, the slot having shoulder portions which prevents linear movement of the scalpel blade of the third type while at the same time allowing linear movement of the portion of a handle of a third type received therein, such linear movement enabling the scalpel blade of the third type to be releasably engaged to the portion of the handle of the third type, the slot of the third type formed through at least one wall portion of the sharps container for causing, upon linear movement of the portion of the handle of the third type while preventing linear movement of the scalpel blade of the third type, single-handed disengagement of the scalpel blade of the third type from the handle of the third type and disposal of the scalpel blade of the third type in the containment volume.

14. The apparatus of claim 13, wherein the slot of the second type comprises a tapered rectangular slot, and the slot of the first type comprises a narrow slot located at a bottom portion of the slot of the second type.

15. The apparatus of claim 13, wherein the wall portion of the sharps container includes at least one slot of the second type positioned at either side of a slot of the first type.

16. The apparatus of claim 13, wherein the sharps container comprises an upper part and a lower part, each part including a corresponding hinge portion, the hinge portions enabling the upper and lower parts to become folded with respect to each other to form the enclosed disposal area.

17. The apparatus of claim 13, wherein the upper part of the sharps container includes a raised wall portion forming a flap and the lower part of the sharps container includes the wall portion with the slot of the first type formed there through, wherein upon folding of the upper and lower parts to form the enclosed disposal area, the flap becomes aligned with the wall portion with the slot of the first type so as to complete the perimeter of the containment volume, thereby preventing escape of contents of the disposal area of the container via the slots.

18. The apparatus of claim 13, further including a foam block adhered within the enclosed disposal area of the sharps container so as to be aligned with a slot of the second type, the foam block providing increased friction to a syringe tip that has pierced the foam block.

19. A method for removal and disposal of a scalpel blade releasably attached to a round scalpel handle via a rotational coupling, comprising positioning the scalpel blade in a slot formed through a perimeter wall portion of a sharps container that defines at least a portion of a containment volume, the slot having a length and a width dimensioned to receive and engage with the scalpel blade therein in a manner so as to prevent rotation of the scalpel blade while at the same time not receive therein any portion of the handle; rotating a handle portion so as to disengage the blade from the handle portion, wherein upon disengagement of the blade from the handle, the blade remains inside the containment volume.

20. The method of claim 19, wherein rotation of the handle causes loosening of a chuck or collet that had engaged the scalpel blade to the handle.

* * * * *